United States Patent [19]
Helland et al.

[11] Patent Number: 5,628,780
[45] Date of Patent: May 13, 1997

[54] PROTECTIVE, VISIBLE SUTURE SLEEVE FOR ANCHORING TRANSVENOUS LEAD BODIES

[75] Inventors: John R. Helland, Santa Clarita; Hong Li, Canyon Country, both of Calif.

[73] Assignee: Pacesetter, Inc., Sylmar, Calif.

[21] Appl. No.: 387,525

[22] Filed: Feb. 13, 1995

Related U.S. Application Data

[63] Continuation of Ser. No. 78,521, Jun. 17, 1993, Pat. No. 5,423,763.

[51] Int. Cl.$^6$ .............................. A61N 1/00; A61N 1/04
[52] U.S. Cl. ................ 607/126; 604/174; 604/175; 604/362; 128/689; 128/DIG. 26
[58] Field of Search ........................... 604/174, 175, 604/362; 607/120, 127, 128, 126; 128/692, 654, DIG. 26

[56] References Cited

U.S. PATENT DOCUMENTS

| | | | |
|---|---|---|---|
| 4,041,931 | 8/1977 | Elliott et al. ................. | 623/1 |
| 4,202,349 | 5/1980 | Jones ........................... | 623/1 |
| 4,516,584 | 5/1985 | Garcia . | |
| 4,553,961 | 11/1985 | Pohndorf et al. . | |
| 4,672,979 | 6/1987 | Pohndorf . | |
| 5,047,050 | 9/1991 | Arpesani ...................... | 623/1 |
| 5,107,856 | 4/1992 | Kristiansen et al. ......... | 128/785 |
| 5,320,100 | 6/1994 | Herweck et al. ............. | 128/654 |

*Primary Examiner*—Michael Powell Buiz
*Assistant Examiner*—Mark S. Leonardo

[57] ABSTRACT

A suture sleeve for anchoring the lead body of an implantable medical device is fabricated of a biocompatible, polymeric material to which has been added color pigment in clear contrast with the bodily tissue adjacent the sleeve. The sleeve is therefore readily visible to the naked eye to aid the physician in locating the sleeve during lead implant or lead revision. Furthermore, the tubular body may be radiopaque and, therefore, easily seen on a fluoroscope through the addition of a radiologically dense material, such as tantalum powder, to the plastic from which the sleeve is molded.

11 Claims, 1 Drawing Sheet

U.S. Patent May 13, 1997 5,628,780 ated application of application Ser. No. 08/078,521, filed Jun. 17, 1993, now U.S. Pat. No. 5,423,763.

PROTECTIVE, VISIBLE SUTURE SLEEVE FOR ANCHORING TRANSVENOUS LEAD BODIES

This is a continuing application of application Ser. No. 08/078,521, filed Jun. 17, 1993, now U.S. Pat. No. 5,423,763.

FIELD OF THE INVENTION

This invention relates to suture sleeves for anchoring the lead bodies used in conjunction with implantable medical devices such as cardiac pacemakers and defibrillators.

BACKGROUND OF THE INVENTION

During the implantation of an endocardial lead body, the lead is introduced into the heart using a venous approach, usually from the subclavian or cephalic vein in the shoulder area under the pectoral muscle. To stabilize the lead body at the venous entry site, the lead body is secured to both the vein and to the surrounding fascia tissue. A suture placed around the vein near the lead entry point ties the lead body to the vein, and a suture sleeve around the lead body is used to anchor the lead body to adjacent tissue.

Suture sleeves in present use are generally tubular structures molded out of a soft, implantable elastomer such as silicone, and which are placed on the lead body during manufacture. After the lead body is implanted and tied to the vein, the sleeve is slid along the lead body to the location at which the lead is to be anchored to the underlying tissue. One or more sutures are then tied around the sleeve to compress it and thereby secure it to the lead body. Circumferential grooves in the outer surface of the sleeve are typically provided for this purpose. The last step is to anchor the sleeve to adjacent body tissue. Sutures may be passed through eyelets formed in a pair of tabs projecting from the sleeve which can provide the required anchoring; or sutures used to secure the sleeve to the lead body can also be used to secure the sleeve and lead body assembly to the underlying tissue.

In the design of suture sleeves, four (4) basic requirements should be met: (1) the sleeve should protect the lead body from high tie-down forces (for example, 6.5 lb. tie force) which might otherwise cause insulation or coil damage; (2) the slip force, that is, the force required to slide the lead body within the sleeve under wet conditions, should be greater than a predetermined minimum, for example, 0.7 lb, for relatively low tie-down forces (of, for example, 4 lbs.); (3) the slip force without the tie-down should be lower than a predetermined maximum, for example, 0.25 lb; and (4) the sleeve, before tie-down, should not fall freely on the lead body when the lead body is held or positioned vertically. These requirements should be met for a wide range of tie-down forces since the tie-down tightness varies among physicians and from implant to implant. And, in all cases, the sleeve must hold the lead body securely in position when tied-down.

The performance of suture sleeves is dependent upon several variables including the strength, elasticity and hardness of the suture sleeve material; the friction coefficient of the sleeve and the lead body; suture sleeve bore to lead body clearance; the stress distribution in the anchoring sleeve from the tie(s); and the strength of the lead body.

Tests have shown that for bipolar coaxial leads, suture sleeves with thick walls provide satisfactory lead body protection when tie-down forces are high. Such sleeves, however, cannot hold lead bodies securely in position under wet conditions (when the lead body is covered with bodily fluids, for example) with low tie-down forces. This is especially a problem with lead bodies coated with a lubricious material such as polyvinylpyrrolidone (PVP). On the other hand, when the wall thickness of the suture sleeve is reduced so that it can hold the lead in position at a low tie-down force under wet conditions, the sleeve is not always able to protect the lead body against insulation or coil damage when the suture tie is very tight.

Accordingly, it is an overall object of the present invention to provide a suture sleeve that reduces tie-down damage, yet holds the lead body securely in place for a wide, practical range of tie-down forces in implant conditions.

Another drawback of presently available suture sleeves is that at the time of lead revision, it is often difficult to locate the suture sleeve when it is encased in fibrous tissue. Present suture sleeves are translucent and are not readily visible to the physician because of lack of color contrast between the sleeve and the surrounding tissue. The physician is often forced to dissect tissue and search along the lead to locate the sleeve. Finding a suture sleeve is thus time-consuming, can be traumatic to the patient, and may cause damage to the lead body which can also make explantation difficult.

It would also be desirable to be able to fluoroscopically observe the suture sleeve so as to ascertain its position and the integrity of the portion of the lead body within the sleeve. Presently available suture sleeves, however, are not visible under fluoroscopy.

It is therefore another object of the invention to provide a suture sleeve that clearly contrasts with adjacent tissue and therefore is easily visible to the naked eye.

A further object of the invention is to provide a suture sleeve that is radiopaque for enhanced fluoroscopic visibility, yet not so radiopaque that the lead body's conductor coil(s) cannot also be seen fluoroscopically.

SUMMARY OF THE INVENTION

In accordance with one specific, exemplary form of the invention, there is provided an anchoring suture sleeve comprising a tubular body having an exterior surface and an interior surface, the latter surface defining a longitudinal through bore for receiving a lead body. The exterior surface defines at least one annular, suture-receiving groove and at least one longitudinally extending or axial groove. The at least one axial groove intersects the at least one annular suture-receiving groove and has ends extending in a longitudinal direction beyond the at least one annular groove. The at least one axial groove enables most of the tie-down forces to be transmitted to the lead body in order to obtain a high slip force (the force required to slide the tied-down sleeve along the lead body) while making it possible to use a thick sleeve wall and relatively hard material to reduce the stress concentrations on the lead body. Further, the at least one axial groove tends to inherently limit the stress applied to the lead body. Once the longitudinal sides of the at least one axial groove come into contact with each other as a result of the compression forces applied to the sleeve by the suture(s), further compression is resisted.

In accordance with another aspect of the invention, the interior surface of the tubular body includes a plurality of inwardly extending projections having rounded surfaces adapted to engage the lead body. The positional relationship between the projections and the rounded surfaces thereof provide less frictional resistance to the movement of the sleeve along the lead body before tie-down yet afford sufficient friction to hold the sleeve in place even with the lead body held vertically.

In accordance with yet another feature of the invention, the tubular body is color pigmented so that the suture sleeve is in clear contrast with the bodily tissue adjacent the sleeve. The sleeve is therefore readily visible to the naked eye to aid the physician in locating the sleeve during lead implant or lead revision. Furthermore, the tubular body may be radiopaque and, therefore, easily seen on a fluoroscope through the addition of a radiologically dense material, such as tantalum powder, to the plastic from which the sleeve is molded.

BRIEF DESCRIPTION OF THE DRAWINGS

Further objects, advantages and features of the invention will become apparent from the detailed description of the preferred embodiments, below, when read in conjunction with the accompanying drawings, in which.

DETAILED DESCRIPTION OF THE PREFERRED EMBODIMENTS

Figure 1:
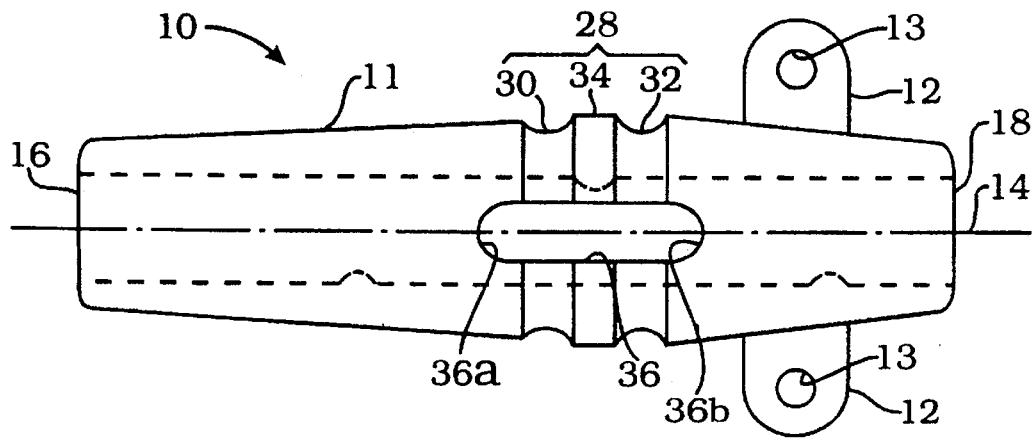
FIG. 1 is a side view of a suture sleeve in accordance with a preferred embodiment of the present invention.
Figure 2:
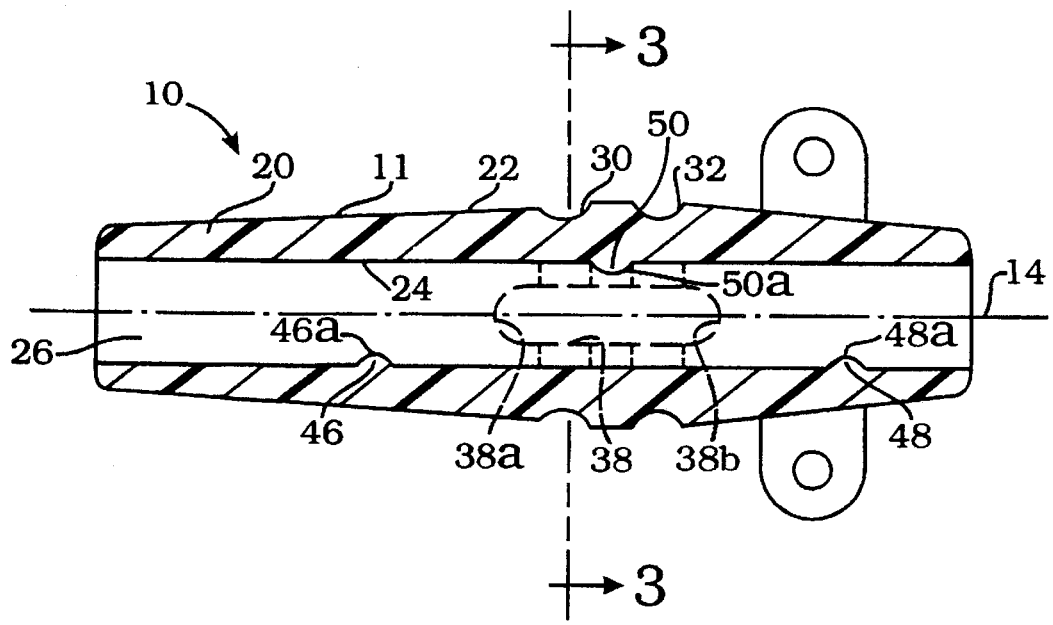
FIG. 2 is an axial cross section view of the suture sleeve of FIG. 1.
Figure 3:
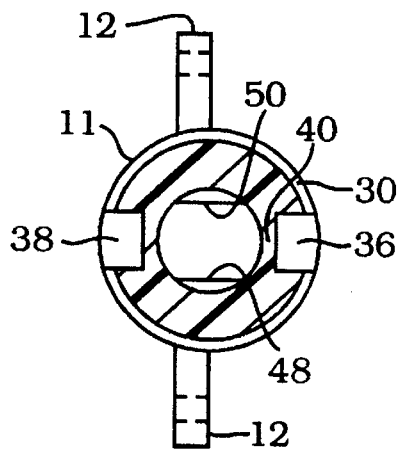
FIG. 3 is a transverse cross section of the suture sleeve of FIGS. 1 and 2 as seen along the line 3—3 in FIG. 2.

FIGS. 1–3 show a suture sleeve 10 in accordance with a preferred embodiment of the invention for gripping and anchoring a lead body of an implantable medical device such as a cardiac pacemaker or implantable defibrillator. Because the structures of lead bodies are well known in the art, a showing thereof has been omitted from the drawings for the sake of simplicity. The lead body will typically be of the bipolar coaxial type with which the present invention has particular utility. As is known, such lead bodies comprise inner and outer coiled conductors surrounded by an outer tube of soft, implantable insulating material such as polyurethane or silicone. As is also known, such bipolar coaxial lead bodies are subject to being damaged as a result of stresses transmitted to the inner insulation and coils thereof because of excessive suture sleeve tie-down forces.

The suture sleeve 10 may be made of peroxide catalyzed (MDX) silicone rubber, extra tear resistant (ETR) platinum catalyzed silicone rubber, polyethylene, polyurethane or any other polymeric, biocompatible, biostable material. The sleeve 10 comprises a tubular body 11 and a pair of projecting tabs 12 formed integrally with the tubular body 11 and having eyelets 13 adapted to receive sutures for tying the suture sleeve 10 to the surrounding tissue.

The tubular body 11 has a central, longitudinal axis 14, opposed ends 16 and 18 and a wall 20 having an exterior surface 22 and an interior surface 24. The interior surface 24 defines an axial through bore 26 adapted to receive the lead body.

The exterior surface 22 of the tubular body 11 includes in a generally central region 28 thereof, a pair of longitudinally spaced apart, circumferential grooves 30 and 32 for receiving the tie-down sutures in a manner well known in the art. Although two such suture receiving grooves are shown it will be understood that this is by way of example only and that, for example, a single groove or more than two grooves may also be utilized. When more than one groove is provided, any one or more of the grooves may be used for tie-down. The grooves 30 and 32 are separated by a short cylindrical portion 34 of the tubular body. The exterior surface 22 tapers inwardly, that is, toward the longitudinal axis 14, from the central region 28 to the tubular body ends 16 and 18.

To protect the lead body when tied-down tightly (for example, with a 6.5 pound force applied to the suture tie-down) the wall 20 of the tubular body 11 is made relatively thick. For example, in accordance with one practical embodiment of the invention in which the diameter of the bore 26 is about 0.103 inch (2.62 mm), the thickness of the wall at the cylindrical portion 34 is about 0.060 inch (1.52 mm).

Diametrically opposed axial grooves 36 and 38 are formed in the exterior surface of the tubular body 11 to provide a degree of compressibility so that the lead body is held securely in place even when tied-down lightly (for example, 4 pounds of force applied to the suture tie-down). The axial grooves 36 and 38 intersect the circumferential suture grooves 30 and 32 and the ends 36a, 36b and 38a, 38b, respectively, of the grooves 36 and 38 extend in a longitudinal direction beyond the central region 28 of the tubular body containing the circumferential grooves.

Figure 4:
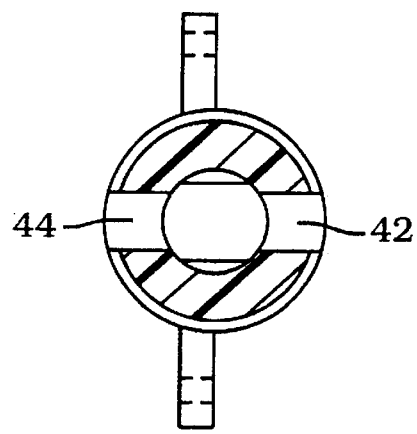
FIG. 4 is a transverse cross section of a suture sleeve in accordance with an alternative embodiment of the invention.

Preferably, the axial grooves 36 and 38 do not extend entirely through the wall of the tubular body 11. In accordance with a practical example of the invention each axial groove 36, 38 has a depth of about 80% of the wall thickness so as to leave a relatively thin, flexible portion 40 of the wall. It will be evident, however, that instead of grooves of limited depth, slots extending through the entire thickness of the wall 20 may be utilized although the fabrication of a sleeve with such slots may be somewhat more difficult. FIG. 4 shows such an alternative sleeve construction which includes a pair of opposed through slots 42 and 44. The axial grooves 36 and 38 enable most of the tie-down forces to be transmitted to the lead body in order to obtain high slip force (the force required to slide the tied-down sleeve along the lead body) while making it possible to use a thick sleeve wall and relatively hard material to reduce the stress concentrations on the lead body. Further, the axial grooves tend to inherently limit the stress applied to the lead body. Once the longitudinal sides of the grooves come into contact with each other as a result of the compression forces applied to the sleeve by the suture(s), further compression is resisted. Still further, although two axial grooves appear to provide optimum performance, only one groove could be used, as well as three or four.

Formed on the interior surface 24 of the tubular body are a plurality of spaced apart projections 46, 48 and 50, preferably identical and which, when the sleeve is slid onto the lead body, provide interfering contact with the lead body and sufficient frictional engagement to keep the sleeve in place when the lead body is held vertically. The projections 46, 48 and 50 are in staggered relationship. That is, projections 46 and 48 are disposed in axial alignment, the projection 46 being positioned between the central region 28 and the end 16 of the tubular body 11 and the projection 48 being positioned between the central region 28 and the end 18 of the tubular body 11. The projection 50 is disposed in the center of the region 28 about midway between the projections 46 and 48 and, as seen in FIG. 3, is diametrically opposed thereto. Each projection 46, 48 and 50 extends along a chord of the bore 26 (FIG. 3) and has a lead body engaging surface 46a, 48a and 50a, respectively, that is rounded in transverse section as best seen in FIG. 2. The staggered relationship between the projections facilitates cooperation between the sleeve and lead bodies of somewhat different diameters resulting from the manufacturing tolerances associated with the outer diameter of the lead body. For leads of somewhat larger size, that is, toward the larger end of the tolerance range, the staggered projections bend the lead body rather than squeezing the lead body which would have a tendency to produce greater friction between the lead body and sleeve. Thus, the staggered relationship between the projections and their rounded surfaces provide less frictional resistance to the movement of the sleeve before tie-down yet afford sufficient friction to hold the sleeve in place even with the lead body positioned vertically.

Compared with existing suture sleeves, sleeves in accordance with the present invention result in substantially lower deformation of leads tied-down tightly, for example, with 6.5 lbs. applied to the tie-down sutures. Furthermore, suture sleeves of the present invention that are tied-down lightly, for example, with a 4 lb. suture tie-down force, have improved slip forces especially when the sleeves were molded of MDX silicone rubber. Moreover, sleeves in accordance with the invention hold lead bodies securely under wet conditions and with or without a lubricious coating such as PVP applied to the outer surface of the lead body insulation. At the same time, untied sleeves in accordance with the invention do not slide along leads held vertically.

In accordance with another aspect of the invention, it was found that the visibility of the suture sleeve to the naked eye can be substantially improved to aid in locating the sleeve after it is implanted and encased in fibrous tissue by adding a biocompatible coloring agent such as titanium dioxide ($TiO_2$) pigment to the suture sleeve material before molding. For example, the addition of 0.2–0.3%, by weight, of $TiO_2$ to MDX silicone rubber to give the sleeve an off white or light gray color provides excellent contrast between the sleeve and the lead body and the adjacent body tissue. The sleeve is therefore highly visible and easily located.

Pursuant to yet another aspect of the invention, to render the suture sleeve more readily visible fluoroscopically, a limited amount of radiologically dense powder is added to the raw plastic mixture. For example, by adding 3–7%, by weight, of tantalum (Ta) powder to the mix, suture sleeves produced thereby are readily distinguishable on a fluoroscope; the image, however, is not so dark as to occlude the lead body conductor coils within the sleeves. Thus, the integrity of the lead body coils under the sleeve after tie-down can be verified. It will be understood that any radiologically dense material can be used; tantalum is, however, preferred because it is both biocompatible and inexpensive. Advantageously, the additions of the $TiO_2$ and Ta to the sleeve do not compromise the mechanical properties of the sleeve.

While various modifications and alternative constructions of the invention will be obvious to those skilled in the art, only specific, preferred embodiments thereof have been shown in the drawings and described in detail. It should be understood, however, that there is no intention to limit the invention to the specific forms or examples illustrated and described. On the contrary, the intention is to cover all modifications, alternative constructions and equivalents falling within the spirit and scope of the invention as defined by the appended claims.

What is claimed is:

1. A suture sleeve for anchoring a lead body of an implantable stimulation lead, the implantable stimulation lead have at least one conductor insulated within the lead body, comprising:

a tubular body having an interior and an exterior surface, the interior surface defining a longitudinal bore dimensioned to receive the lead body of the implantable stimulation lead, the exterior surface having at least one annular, suture-receiving groove, the tubular body being formed of biocompatible polymeric material with a predetermined amount of radiologically dense powder dispersed therein so as to present a clear fluoroscopic image, whereby the sleeve can be fluoroscopically located on the lead body.

2. The suture sleeve, as recited in claim 1, wherein:

the predetermined amount of radiologically dense powder is an amount which presents a clear fluoroscopic image without being so dark that it occludes the at least one conductor within the lead body in the area of the suture sleeve;

whereby the integrity of the at least one conductor received within the suture sleeve can be verified after the suture sleeve is tied down.

3. The suture sleeve, as recited in claim 2, wherein the radiologically dense powder is tantalum powder.

4. The suture sleeve, as recited in claim 3, wherein the predetermined amount of radiologically dense powder is 3–7%, by weight, of tantalum powder.

5. A suture sleeve for anchoring a lead body of an implantable stimulation lead, comprising:

a tubular body having an interior and an exterior surface, the interior surface defining a longitudinal bore dimensioned to receive the lead body of the implantable stimulation lead, the exterior surface having at least one annular, suture-receiving groove, the tubular body being formed of biocompatible polymeric material with a predetermined amount of pigment dispersed therein so as to contrast with that of adjacent body tissue, whereby the sleeve can be readily visible to the naked eye to aid in its location on the stimulation lead.

6. The suture sleeve, as recited in claim 5, wherein the pigment is titanium dioxide pigment.

7. The suture sleeve, as recited in claim 6, wherein the predetermined amount of pigment is 0.2–0.3%, by weight, of titanium dioxide pigment.

8. A suture sleeve for anchoring a implantable stimulation lead, the implantable stimulation lead having a conductor coil therein, the suture sleeve comprising:

a tubular body having an interior and an exterior surface, the interior surface defining a longitudinal bore dimensioned to receive the lead body of the implantable stimulation lead, the exterior surface having at least one annular, suture-receiving groove, the tubular body being formed of a radiopaque, biocompatible polymeric material so as to present a clear fluoroscopic image without being so dark that it occludes the conductor coil within the sleeve;

whereby the sleeve can be fluoroscopically located on the lead body and the integrity of the conductor coil received within the suture sleeve can be verified after the lead body is tied down.

9. A suture sleeve for anchoring a lead body of an implantable stimulation lead to body tissue, the implantable stimulation lead having a conductor coil insulated within the lead body, comprising:

a tubular body having an interior and an exterior surface, the interior surface having means for receiving the lead body of the implantable stimulation lead; and securing means, on the exterior surface of the tubular body, for securing the tubular body to selected body tissue;

wherein the tubular body is molded of a radiopaque, biocompatible polymeric material so as to present a clear fluoroscopic image for locating the tubular body on the stimulation lead in the body tissue.

10. The suture sleeve, as recited in claim 9, wherein: the radiopaque, biocompatible polymeric material has sufficient radiopaque material so as to present a clear fluoroscopic image without being so dark that it occludes the conductor coil within the sleeve;

whereby the integrity of the conductor coil received within the suture sleeve can be verified after the lead body is tied down.

11. A suture sleeve for anchoring a lead body of an implantable stimulation lead to body tissue, comprising:

a tubular body having an interior and an exterior surface, the interior surface having means for receiving the lead body of the implantable stimulation lead; and securing means, on the exterior surface of the tubular body, for securing the tubular body to selected body tissue;

wherein the tubular body is molded of a pigmented, biocompatible polymeric material which contrasts with that of adjacent body tissue for locating the tubular body along the stimulation lead in the body tissue.

* * * * *